US006989744B2

(12) United States Patent
Proebsting (10) Patent No.: US 6,989,744 B2
(45) Date of Patent: Jan. 24, 2006

(54) INFANT MONITORING SYSTEM WITH REMOVABLE EAR INSERT

(76) Inventor: James R. Proebsting, N52 W16212 Creekwood Crossing, Menomonee Falls, WI (US) 53051

( * ) Notice: Subject to any disclaimer, the term of this patent is extended or adjusted under 35 U.S.C. 154(b) by 0 days.

(21) Appl. No.: 10/461,221

(22) Filed: Jun. 13, 2003

(65) Prior Publication Data

US 2004/0257233 A1    Dec. 23, 2004

(51) Int. Cl.
G08B 1/08    (2006.01)
(52) U.S. Cl. .............................. 340/539.15; 340/539.1; 340/573.1; 340/825.19; 381/315; 381/328
(58) Field of Classification Search ........... 340/539.15, 340/539.1, 573.1, 825.19, 384.1; 381/312, 381/315, 328
See application file for complete search history.

(56) References Cited

U.S. PATENT DOCUMENTS

| 3,819,860 | A | * | 6/1974 | Miller ......................... 381/380 |
| 3,998,209 | A |   | 12/1976 | Macvaugh ..................... 128/1 |
| 4,492,279 | A |   | 1/1985 | Speckhart ..................... 177/45 |
| 4,644,330 | A |   | 2/1987 | Dowling ...................... 340/575 |
| 4,777,474 | A | * | 10/1988 | Clayton ................. 340/539.11 |
| 4,899,135 | A |   | 2/1990 | Ghahariiran ................ 340/573 |
| 4,920,570 | A | * | 4/1990 | West et al. .................. 381/315 |
| 5,119,072 | A |   | 6/1992 | Hemingway ................ 340/573 |
| 5,142,587 | A |   | 8/1992 | Kobayashi ................... 381/187 |
| 5,210,532 | A |   | 5/1993 | Knoedler et al. ...... 340/825.69 |
| 5,280,635 | A |   | 1/1994 | Knoedler et al. ........... 455/128 |
| 5,343,532 | A | * | 8/1994 | Shugart, III ................ 381/315 |
| 5,420,930 | A | * | 5/1995 | Shugart, III ................ 381/315 |
| 5,446,934 | A |   | 9/1995 | Frazier .......................... 5/655 |
| 5,477,867 | A |   | 12/1995 | Balkanyi .................... 128/848 |
| 5,479,932 | A |   | 1/1996 | Higgins et al. ............. 128/671 |
| 5,505,199 | A |   | 4/1996 | Kim ............................ 128/633 |
| 5,515,865 | A |   | 5/1996 | Scanlon ...................... 128/721 |
| 5,640,147 | A | * | 6/1997 | Chek et al. ............... 340/573.4 |
| 5,689,240 | A |   | 11/1997 | Traxler ....................... 340/573 |
| 5,712,453 | A |   | 1/1998 | Bungardt et al. ........... 181/135 |
| 5,737,692 | A |   | 4/1998 | Lang ............................ 455/66 |
| 5,774,055 | A |   | 6/1998 | Pomerantz .................. 340/573 |
| 5,812,056 | A |   | 9/1998 | Law ........................... 340/539 |
| 5,841,352 | A |   | 11/1998 | Prakash ...................... 340/573 |
| 5,894,455 | A |   | 4/1999 | Sikes .......................... 368/12 |
| 5,900,817 | A |   | 5/1999 | Olmassakian ............ 340/573.1 |
| 5,914,660 | A |   | 6/1999 | Mesibov et al. ............ 340/573 |
| 5,953,435 | A | * | 9/1999 | Mullin et al. ............... 381/380 |
| 5,991,637 | A | * | 11/1999 | Mack et al. ................. 455/563 |
| 6,043,747 | A |   | 3/2000 | Altenhofen ............. 340/573.1 |
| 6,054,926 | A |   | 4/2000 | Deleo ...................... 340/573.1 |

(Continued)

FOREIGN PATENT DOCUMENTS

EP        0 145 160 A3    6/1985

*Primary Examiner*—Daryl C. Pope (57) ABSTRACT

An infant monitoring system contains a removable ear insert. The ear insert receives an audible parameter from an infant in an infant's room and provides the parameter to a parent monitoring device in a parents' room. The parent monitoring device comprises the removable ear insert, whereby only the wearer of the insert is alerted to the audible parameter, without disturbing others nearby the wearer. Individuals near the wearer are not exposed to, or otherwise made aware of, the audible parameter, thereby providing an audio stimulus that is personal to the wearer of the insert. Preferably, the ear insert is comfortably inserted into and worn within the ear of the wearer for use in conjunction with the infant monitoring system, whereby non-wearers of the ear insert remain undisturbed.

43 Claims, 3 Drawing Sheets

U.S. PATENT DOCUMENTS

| | | | |
|---|---|---|---|
| 6,067,006 A * | 5/2000 | O'Brien | 340/384.1 |
| 6,072,392 A | 6/2000 | Henderson et al. | 340/539 |
| 6,118,882 A * | 9/2000 | Haynes | 381/374 |
| 6,150,941 A | 11/2000 | Geiger et al. | 340/573.1 |
| 6,195,009 B1 | 2/2001 | Irizarry et al. | 340/573.4 |
| 6,208,897 B1 | 3/2001 | Jorgenson et al. | 607/5 |
| 6,280,392 B1 | 8/2001 | Yoshimi et al. | 600/534 |
| 6,396,403 B1 | 5/2002 | Haner | 340/573.4 |
| 6,462,664 B1 | 10/2002 | Cuijpers et al. | 340/573.1 |
| 6,542,721 B2 * | 4/2003 | Boesen | 455/553.1 |

* cited by examiner

FIG. 1

(PRIOR ART)

INFANT MONITORING SYSTEM WITH REMOVABLE EAR INSERT

CROSS-REFERENCES TO RELATED APPLICATIONS

—

STATEMENT REGARDING FEDERALLY SPONSORED RESEARCH OR DEVELOPMENT

—

REFERENCE TO MICROFICHE APPENDIX

—

BACKGROUND OF THE INVENTION

1. Field of the Invention

The present invention relates generally to infant monitoring systems, and more particularly, to infant monitoring systems providing personal alerts to a user without disturbing others nearby the user.

2. Description of Related Art

Intra-Concha Devices

Various types of headset devices have been described, including some of which fit into a wearer's ear. For example, U.S. Pat. No. 5,142,587, issued on Aug. 25, 1992 to Kobayashi, discloses an intra-concha type electroacoustic transducer for use with audio devices. More specifically, it recognizes an intra-concha type electroacoustic transducer comprising a housing for accommodating a speaker unit therein. The transducer includes a diaphragm that is detachably mounted to the concha of a user's ear, whereby the diaphragm of the speaker unit is disposed so as to oppose the entrance portion of the external auditory meatus of the user's ear. An auxiliary means projects from the housing in a direction that is opposite to the entrance portion of the external auditory meatus. It supports the housing when the transducer is in a mounted position within the user's ear.

U.S. Pat. No. 5,712,453, issued on Jan. 27, 1998 to Bungardt et al., discloses an apparatus for stabilizing a concha style headset. More specifically, it describes a stabilizer comprising a receiver attachment and a concha stabilizer pad. The concha stabilizer pad is secured to a receiver attachment by a flexible supporting member and engages the wearer's upper concha beneath the antihelex when the receiver is placed in the wearer's lower concha between the tragus and antitragus, thereby creating three points of contact, namely the tragus, anti-tragus, and upper concha. Alternatively, the stabilizer is formed from an arch that connects to the receiver, and is disposed upward from the receiver. In an alternative embodiment, the stabilizer is formed as a torus (i.e., ring-shaped) that is coupled to a stalk-shaped supporting member.

U.S. Pat. No. 5,953,435, issued on Sep. 14, 1999 to Mullin et al., discloses an intra-concha stabilizer with a length-wise adjustable conchal wall hook that positions an audio transducer (i.e., a speaker) within a wearer's ear without requiring a headband or behind-the-ear hook. By engaging the conchal wall of the wearer's ear, the conchal wall hook secures the audio speaker within the wearer's ear. More specifically, the audio transducer is positioned within the ear between the tragus and antitragus, whereupon the wearer slides a conchal wall hook carrier and conchal wall hook. The wearer repeats this action until the conchal wall hook preferably engages the conchal wall of the wearer's ear. The conchal wall hook carrier is purportedly of a size to fit snugly into the groove so that it will not slip or move without pressure being applied thereto. As described, by positioning the conchal wall hook securely against the conchal wall of the wearer's ear, the stabilizer prevents the audio transducer from moving within, or falling out of, the wearer's ear, and purportedly provides sufficient force to hold the audio speaker against the lower concha of the wearer's ear.

Anti-Snoring Devices

Many types of sleep monitoring devices have been described, including anti-snoring devices. For example, U.S. Pat. No. 3,998,209, issued on Dec. 21, 1976 to Macvaugh, discloses a snoring deconditioning system and method whereby a control console activates various aversive stimuli sources—including a globally projected pillow buzzer—when snoring exceeds a predetermined auditory level.

U.S. Pat. No. 4,644,330, issued on Feb. 17, 1987 to Dowling, and published as EP 0 145 160 A3 on Jun. 19, 1985, discloses a compact, self-contained anti-snoring device that either mounts on the ear of a user or fits therewithin. Since the speaker means either mounts on the ear of a user or fits therewithin, the anti-snoring stimulus is purportedly personal to the user so as to not disturb the snorer's bed partner.

U.S. Pat. No. 5,477,867, issued on Dec. 26, 1995 to Balkanyi, discloses a snoring suppression device that emits an audible sound. While a housing of the device is normally placed on a bedside table of the sleeper, it recognizes that the acoustic signal should not be generated on the table if the snoring person does not sleep alone—i.e., it recognizes that the signal should be generated close to the sleeper, e.g., at the sleeper's forehead or temple, or alternatively, as a compact unit that fits into the sleeper's ear. However, it further recognizes that positioning such a device in or behind the ear is often found to be uncomfortable, especially if the sleeper lies on that ear. For these reasons, an arrangement of the device in a headband is preferred.

While some anti-snoring devices fit within the outer ear of the wearer, they are all designed to monitor sounds within the same room as the wearer, and some alert the snoring party before a bed partner is aroused by the snoring.

Alarm Clock Devices

Other types of monitoring devices have been described. For example, U.S. Pat. No. 5,737,692, issued on Apr. 7, 1998 to Lang, discloses a clock radio system with a wireless remote alert device, in which radio signals from a clock radio purportedly alert a user at a predetermined time without disturbing others. As described, the device is similar in design to an earplug and is inserted in the user's ear, or worn or carried as a bracelet, wherein an object of the device is to alert the user at a predetermined time without disturbing others. The user is directed to insert the device into the user's ear before going to sleep, whereupon only the user is purportedly awakened as the device is actuated, and no one else is thereby disturbed. It is also disclosed that a second user can assert a second, different wireless remote alert device in the second user's ear before going to sleep, whereby, purportedly, only the first user is awakened by the wireless remote alert device in response to a first alarm and only the second user is awakened by the wireless remote alert device in response to a second alarm.

U.S. Pat. No. 5,894,455, issued on Apr. 13, 1999 to Sikes, discloses an alarm clock system that includes a conventional speaker output for sounding a general wake-up alarm and an ear insert having an audible output that is inserted into the ear of a person needing to be awaken when only one person needs to be awoken. It recognizes that many individuals share a bed with a spouse, or a room with another person, who are awoken or disturbed when an alarm clock sounds a general wake-up alarm that is only needed by one of the people. It therefore discloses an alarm clock system that includes an ear insert having an audible output that is inserted only into the ear of the person needing to be awoken. Because all of the people sleeping in the room must be awoken at the same time on some days, it thus also recognizes that it would be further beneficial to have such an alarm clock system that includes a convention speaker output for sounding a general wake-up alarm.

U.S. Pat. No. 6,067,006, issued on May 23, 2000 to O'Brien, discloses an audible alarm device that is intended to personally alert a user to an alarm, time of day, or other status condition. The device is implemented in the form of a molded earplug made of rubber, silicone, or another material suitable for being inserted into, or covering, an ear. It discloses the following as common status conditions: time of day, time to wake up, phone messages waiting to be heard, etc.

Baby Monitoring Devices

Finally, baby monitoring devices have also been described. For example, U.S. Pat. No. 6,043,747, issued on Mar. 28, 2000 to Altenhofen, discloses a baby monitor system that includes a parent monitor and a baby monitor that have a two-way radio frequency communications link established therebetween. From the parent monitor, the system allows a caregiver to transmit a prerecorded soothing message for playback to an infant or child through the baby monitor when the caregiver is in an environment, such as a shower, wherein ambient noises would tend to startle, irritate, or disturb the recipient child. Accordingly, the system includes a message storage mechanism for recording the soothing message, and a playing mechanism for playing the soothing message in response to an activation signal. Because the caregiver's intended use of the parent monitor is while bathing, the parent monitor is preferably waterproof.

U.S. Pat. No. 6,150,941, issued on Nov. 21, 2000 to Geiger et al., discloses a stand-off non-invasive acoustic baby monitor for preventing Sudden Infant Death Syndrome ("SIDS"). More specifically, it discloses an apnea monitor that reduces false alarms without having to physically contact a child or infant, whereby if a resultant signal—which corresponds to continuous breathing or physical activity—deviates substantially from a comparator signal for a sufficient length of time, an alarm is activated to signal either abnormal breathing activity or a lack of breathing activity. A lack of breathing activity indicates either a medical condition, such as the on-set of SIDS, or a child's absence from a monitored area.

U.S. Pat. No. 6,208,897, issued on Mar. 27, 2001 to Jorgensen et al., also discloses a SIDS prevention baby monitor that monitors the respiration or cardiac activity of an infant identified with Long QT Syndrome resulting from structural abnormalities in potassium channels of a child's heart, which predispose the child to an accelerated heart rhythm (i.e., arrhythmia). It recognizes a link between SIDS and Long QT Syndrome and provides a mechanism for use in initiating treatment until medical personnel arrive.

U.S. Pat. No. 6,462,664, issued on Oct. 8, 2002 to Cuijpers et al., discloses a baby monitor that controls the volume level of an external, electronic device when an output sound level of a receiver reaches a predetermined reference level. More specifically, the baby monitor is capable of muting a television, or other electronic device, through an infrared command signal, thus allowing a parent to hear the output sound of the baby monitor over the other device.

Numerous other baby monitors have also been described, including, for example, U.S. Pat. No. 4,492,279, issued on Jan. 8, 1985 to Speckhart; U.S. Pat. No. 4,899,135, issued on Feb. 6, 1990 to Ghahariiran; U.S. Pat. No. 5,119,072, issued on Jun. 2, 1992 to Hemingway; U.S. Pat. No. 5,210,532, issued on May 11, 1993 to Knoedler et al.; U.S. Pat. No. 5,280,635, issued on Jan. 18, 1994 to Knoedler et al.; U.S. Pat. No. 5,446,934, issued on Sep. 5, 1995 to Frazier; U.S. Pat. No. 5,479,932, issued on Jan. 2, 1996 to Higgins et al.; U.S. Pat. No. 5,505,199, issued on Apr. 9, 1996 to Kim; U.S. Pat. No. 5,515,865, issued on May 14, 1996 to Scanlon; U.S. Pat. No. 5,640,147, issued on Jun. 17, 1997 to Chek et al.; U.S. Pat. No. 5,689,240, issued on Nov. 18, 1997 to Traxler; U.S. Pat. No. 5,774,055, issued on Jun. 30, 1998 to Pomerantz; U.S. Pat. No. 5,812,056, issued on Sep. 22, 1998 to Law; U.S. Pat. No. 5,841,352, issued on Nov. 24, 1998 to Prakash; U.S. Pat. No. 5,900,817, issued on May 4, 1999 to Olmassakian; U.S. Pat. No. 5,914,660, issued on Jun. 22, 1999 to Mesibov et al.; U.S. Pat. No. 6,054,926, issued on Apr. 25, 2000 to Deleo; U.S. Pat. No. 6,072,392, issued on Jun. 6, 2000 to Henderson et al.; U.S. Pat. No. 6,195,009, issued on Feb. 27, 2001 to Irizarry et al.; U.S. Pat. No. 6,280,392, issued on Aug. 28, 2001 to Yoshimi et al.; and U.S. Pat. No. 6,396,403, issued on May 28, 2002 to Haner.

Several of the foregoing U.S. patents attempted partial solutions to some of the foregoing concerns, some of which were, occasionally, and in part, satisfactory for the limited purposes for which they were intended. Accordingly, each of the foregoing U.S. patents are hereby incorporated by reference, in their entireties, into the present application for purposes including, but not limited to, indicating the background of the present invention and illustrating the state of the art. However, many related art solutions have been implemented with less-than-overwhelming success. Thus, for example, what is needed is infant monitoring system with a removable ear insert.

BRIEF SUMMARY OF THE INVENTION

By way of general summary, inventive arrangements are directed to improved infant monitoring systems. By way of more specific summary, inventive arrangements are directed to an infant monitoring system with a removable ear insert. The ear insert receives an audible parameter from an infant in an infant's room and provides the parameter to a parent monitoring device in a parents' room. The parent monitoring device comprises the removable ear insert, whereby only the wearer of the insert is preferably alerted to the audible parameter.

In a preferred embodiment, the insert is inserted into an ear of a parent, or other caregiver, needing to be awoken, whereby only effected persons are alerted to audible parameters from the infant in the infant's room. Accordingly, only the wearer of the ear insert is awoken without disturbing others nearby the wearer who are not wearing the insert. Without a globally broadcast audible parameter emanating from a loudspeaker and sound grating of a conventional parent monitoring device, individuals near the wearer are preferably not exposed to, or otherwise made aware of, the audible parameter, thereby providing an audio stimulus that is personal to the wearer of the insert. Thus, the invention provides an ear insert that is comfortably inserted into and worn within the ear of the wearer for use in conjunction with an infant monitoring system, whereby non-wearers of the ear insert remain undisturbed.

BRIEF DESCRIPTION OF THE SEVERAL VIEWS OF THE DRAWINGS

Many facets of the invention will be better appreciated and understood in conjunction with the following drawings and detailed description of preferred embodiments, in which like reference numerals generally represent like elements, and in which.

DETAILED DESCRIPTION OF PREFERRED EMBODIMENTS

Various systems, apparatuses, devices, methods, techniques, and the like for remotely monitoring the presence and general well-being of babies, infants, toddlers, and other children when out of plain view by caregivers are well-known in the art, and for ease of illustration, are generally and generically referred to as infant monitoring systems throughout this Specification. However, the present invention is not limited in this regard. Rather, in various preferred embodiments, for example, the inventive arrangements are also used to monitor other persons, including, for example, persons who are elderly, sick, infirm, or otherwise in need of monitoring, particularly, but not exclusively, while sleeping. In various other preferred embodiments, the inventive arrangements are also used to monitor other things, including, for example, animals, and the like, when a personal alert to a caregiver, or other user, is desired.

Figure 1:
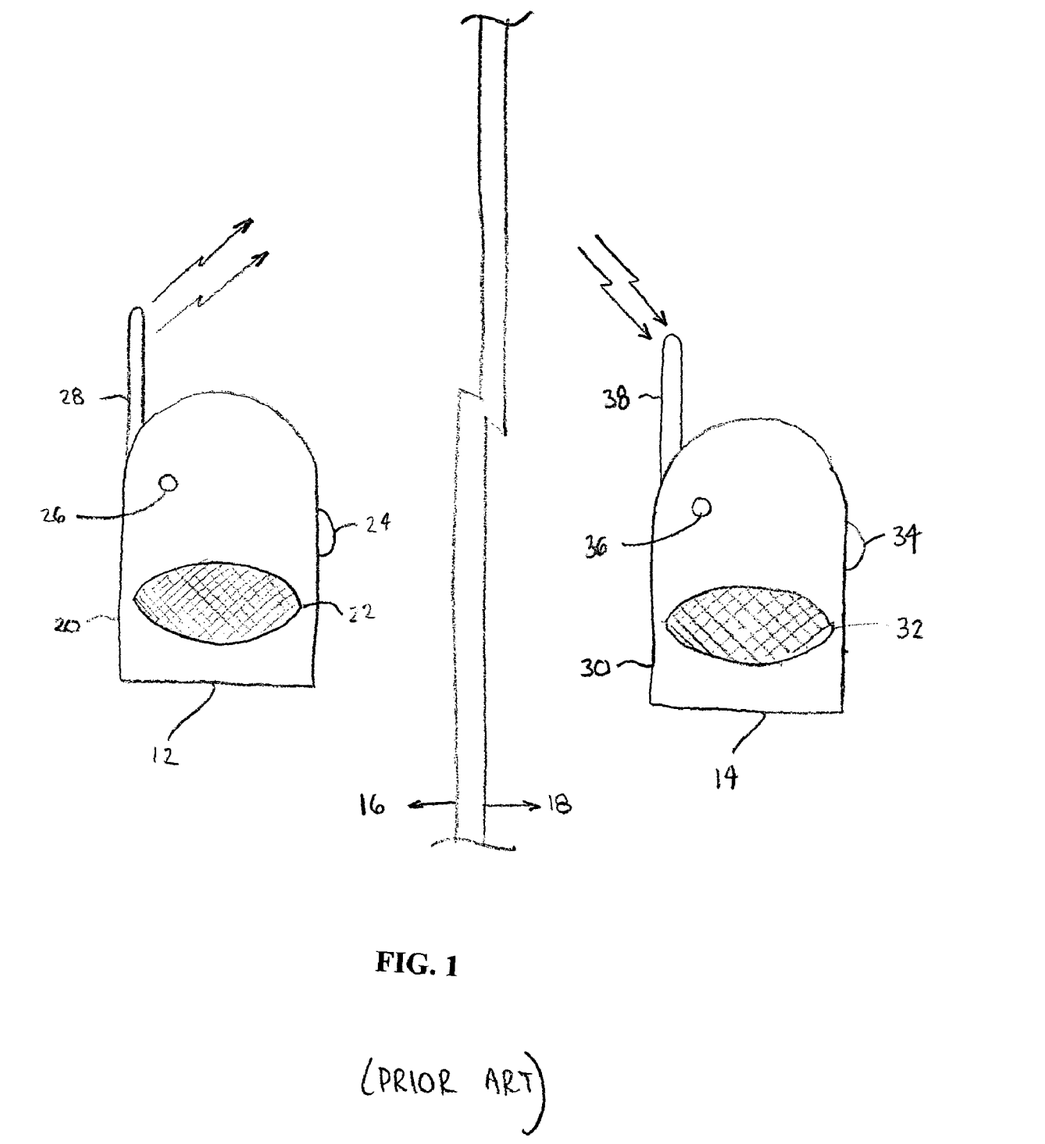
FIG. 1 depicts a conventional infant monitoring system.

Referring now to FIG. 1, a conventional infant monitoring system 10 is shown, comprising an infant monitoring device ("IMD") 12 and a parent monitoring device ("PMD") 14. The IMD 12 is generally placed in an infant's room 16, while the PMD 14 is generally placed in a parents' room 18. Whereas the infant's room 16 is generally remote from the parents' room 18, the IMD 12 is generally remote from the PMD 14. As known, wireless transmission occurs therebetween, as will be elaborated upon briefly. Throughout this description, however, certain well-known functions and constructions are not described in detail if they would otherwise obscure the invention in unnecessary detail.

Referring now more specifically to the IMD 12, it comprises a main body 20 with orifices for, and connections to and among, a sound grating 22, on-off/volume variable resistor dial 24, power indicator light 26, and antenna 28. Internally, the IMD 12 comprises a microphone and transmitter. The microphone is a well-known device for converting audible sound waves into electrical current signals. Relevant sound waves comprise an audible parameter from an infant 44 (see FIG. 2) in the infant's room 16, such as a cry, yell, shout, moan, fuss, sneeze, cough, hiccup, wake-up activities, hunger and thirst indicators, out-of-bed or out-of-area indicators, bedding entanglement indicators, and so forth, from the infant 44 communicating discomfort, distress, malcontent, or otherwise to anyone who is listening. Thus, while the sound grating 22 facilitates reception of the audible parameter from the infant 44 by the microphone, the IMD 12 is preferably powered by a conventional power source—such as a household A/C current source, battery, battery cell, or otherwise—operating in conjunction with the on-off/volume variable resistor dial 24, for which the preferred power indicator light 26 conventionally indicates the energized status of the IMD 12.

As mentioned, the microphone converts the audible parameter from the infant 44 into an electrical current signal. More specifically, the magnitude of the voltage of this electrical current signal is directly proportional to the volume (i.e., pitch or pressure) of the audible parameter, and it changes at the same rate (i.e., frequency) as the audible parameter. Thus, the voltage of this electrical current signal changes according to the audible parameter, whereupon the electrical current signal is wirelessly transmitted by the well-known transmitter through the antenna 28 of the IMD 12 in the infant's room 16 to the PMD 14 in the parents' room 18 for real-time reception thereof by the PMD 14.

Referring now more specifically to the PMD 14, it also comprises, as a counterpart to the IMD 12, a main body 30 with orifices for, and connections to and among, a sound grating 32, on-off/volume variable resistor dial 34, power indicator light 36, and antenna 38. Internally, the PMD 14 comprises a receiver and transducer. The transducer is a well-known device for re-converting the electrical current signal received from the antenna 28 of the IMD 12 at the antenna 38 of the PMD 14 back into audible sound waves. Thus, while the sound grating 32 facilitates re-broadcasting the audible parameter from the infant 44 into the parents' room 18, the PMD 14 is preferably powered by a conventional power source—such as a household A/C current source, battery, battery cell, or otherwise—operating in conjunction with the on-off/volume variable resistor dial 34, for which the preferred power indicator light 36 conventionally indicates the energized status of the PMD 14.

As mentioned, the transducer re-converts the electrical current signal from the IMD 12 into the audible parameter from the infant 44. More specifically, the transducer comprises a loudspeaker for transforming the electrical current signal into sound energy. The loudspeaker is a well-known device for transforming the weakened electrical current signals that strike the antenna 38 of the PMD 14 into audible sounds that are heard at a distance remote from the PMD 14. Whereas the weakened electrical current signals are processed by an amplifier, the common loudspeaker contains a cone that is rigidly attached to a coil of wire. The coil of wire is surrounded by a permanent magnet that creates a permanent magnetic field about the coil. However, as electrical current signals from the antenna 38 of the PMD 14 pass through the coil of wire, a varying magnetic field is also induced about the coil. The permanent and varying magnetic fields thus oppose, and otherwise interact, with one another, whereupon the cone thus vibrates according to the variations in the electrical current signals. Successfully vibrating the cone according to the voltage of the original electrical current signal transmitted from the IMD 12, the cone thereby causes surrounding air to vibrate at the same frequencies as the original sound waves. This sound is then broadcast through the sound grating 32 and into the parents' room 18.

Accordingly, the PMD 14 wirelessly reproduces the audible parameter from the infant 44 received by the IMD 12 in the infant's room 16 through the PMD 14 in the parents' room 18.

In other words, if the infant 44 makes a sound within the infant's room 16, the microphone within the IMD 12 detects the sound and transmits it through the antenna 28. The PMD 14, in turn, receives the transmitted signal from the IMD 12 through its antenna 38, where it is processed and output by the transducer, and where it is heard through the loudspeaker for appropriate response thereto by the infant's parents 42 (see FIG. 2).

Many variations of the described infant monitoring system 10 have been described. For example, the main bodies 20, 30, sound gratings 22, 32, on-off/volume variable resistor dials 24, 34, power indicator lights 26, 36, and antennas 28, 38 were representatively depicted and described. Numerous variations—as to existence, location, functionality, and the like—exist with respect thereto. For example, whereas the antennas 28, 38 are respectively integrated within the main bodies 20, 30 in various preferred embodiments, the on-off/volume variable resistor dials 24, 34 are also respectively integrated with the power indicator lights 26, 36 in other preferred embodiments. Regardless, the power supplies preferably enable mobility of both the IMD 12 and PMD 14, and particularly the PMD 14 when used other than in the parents' room 18.

Whereas the IMD 12 has been generally described as a one-way transmitter and the PMD 14 has been generally described as a one-way receiver, the infant monitoring system 10 is not limited in this regard. Rather, two-way communicative abilities are also contemplated, and well-known in the art, whereupon both the IMD 12 and PMD 14 are constructed as transmitters and receivers. For example, if the PMD 14 functions as both a transmitter and receiver, an optional "talk button" (not shown) is incorporated into the housing 30 for ceasing PMD 14 functioning as a receiver and enabling PMD 14 functioning as a transmitter. In such an embodiment, whereas the IMD 12 is generally an open channel transmitter—transmitting continually from the IMD 12 to the PMD 14 while energized—activation of the talk button on the PMD 14 enables transmission from the PMD 14 to the IMD 12 and corresponding reception by the IMD 12 from the PMD 14. Thus, the IMD 12 also thereby functions as a receiver and the PMD 14 also thereby functions as a transmitter. Accordingly, the IMD 12 and PMD 14 are generally and generically referred to, and constructed as, transceivers.

Moreover, in additionally preferred embodiments, the PMD 14 also includes one or more light emitting diodes ("LEDs") (not shown) that light in series to indicate the volume of the audible parameter from the infant 44 in the infant's room 16. In yet another embodiment, the LEDs are color coded such that subsequently lit or higher sounding LEDs are a different color (e.g., red) from previously lit or lower sounding LEDs (e.g., green or yellow or both).

Furthermore, in other additionally preferred embodiments, either or both of the IMD 12 and PMD 14 contain appropriate circuitry for processing an audible parameter from an infant 44 only after detection of a sound level that, as determined by an appropriate comparator: i) deviates substantially from a predetermined reference signal; ii) is greater than a predetermined reference volume level; iii) indicates a lack of presence of the infant 44; iv) indicates a lack of motion of the infant 44; v) indicates a predetermined pattern of motion; vi) monitors for SIDS; vii) responds according to predetermined audible parameters, but otherwise filters out other audible parameters, enabling the infant monitoring system 10 to be particularly responsive to various audible parameters from the infant 44 and less responsive to ambient noises and other external sounds typically occurring in a household setting; viii) falls within, or outside of, various predetermined parameters in accordance with one or more appropriate filters, such as a low pass filter or narrow band bypass filter; ix) does one or more of the foregoing for a predetermined length of time; and the like. In other words, various well-known filtering techniques are preferably incorporated into the infant monitoring system 10 within the scope of the invention without departing from the spirit hereof. All such representative functionality is readily imparted into the infant monitoring system 10 by various techniques that are well-known in the art, including, for example, including the comparator within the IMD 12, PMD 14, or both.

Figure 2:
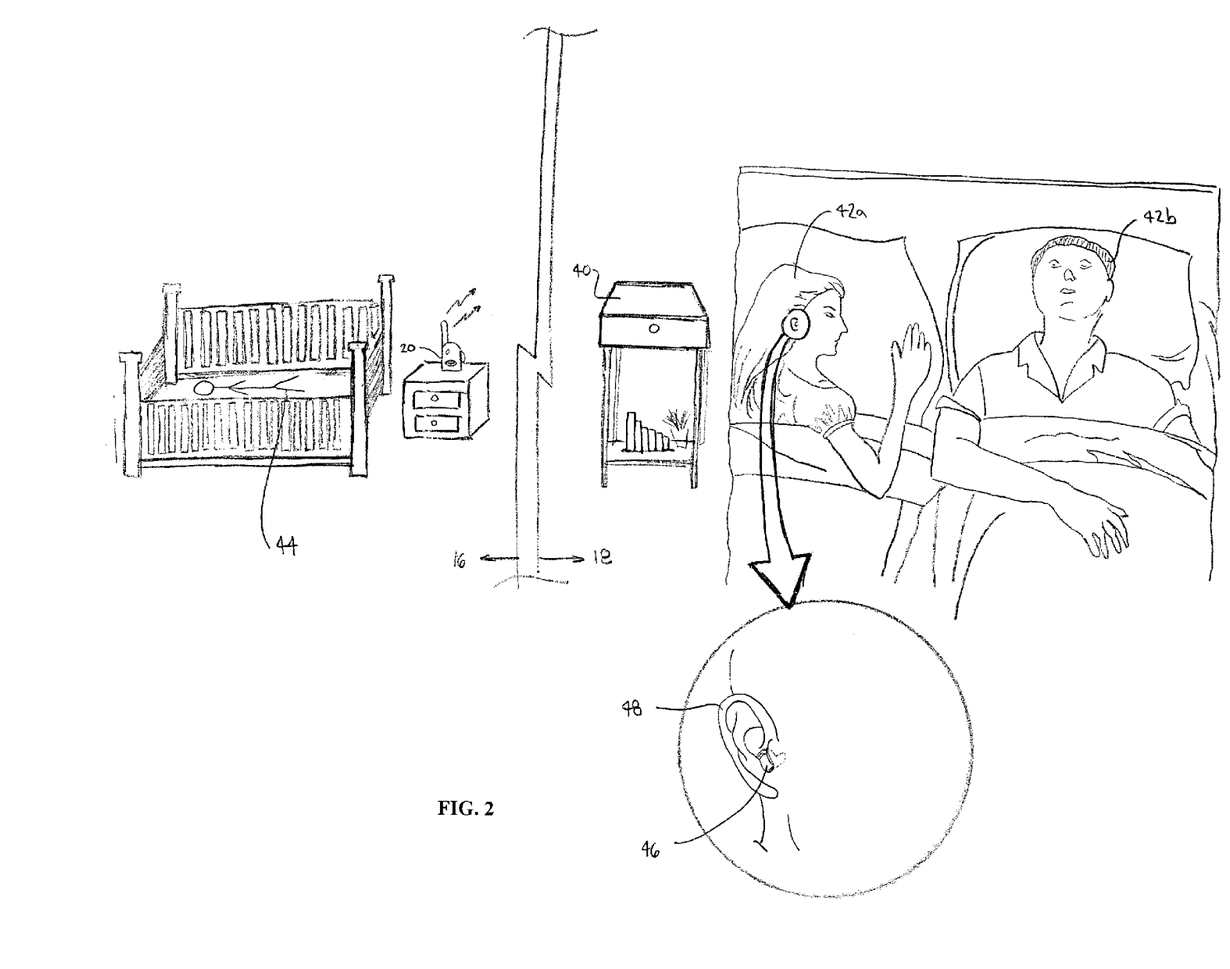
FIG. 2 depicts an infant monitoring system according to preferred embodiments of the inventive arrangements.

Referring now to an infant monitoring system 10 according to preferred embodiments of the inventive arrangements, and FIG. 2, insofar as conventional placement of the PMD 14 is on a bedside table 40, or the like, in the parents' room 18, it is recognized that both of the infant's parents 42 (individually, 42*a* or 42*b*), or other caregivers, are awoken by the globally broadcast audible parameter emanating from the loudspeaker and sound grating 32 of the conventional PMD 14. Oftentimes, however, it is only necessary to awaken one parent 42*a*, 42*b* to appropriately respond to the needs of the infant 44. For example, if only one parent 42*a*, 42*b* is needed to feed or change the infant 44, there is oftentimes little, if any, reason to awaken both parents 42. Thus, it is beneficial to provide a PMD 14 in which only selective persons are alerted to the audible parameter from the infant 44. The infant's parents 42 could thereby alternate nights or weeks, for example, responding to the infant 44 in accordance with work schedules and the like, whereby only one parent 42*a*, 42*b* in the parents' room 18 is alerted to the audible parameter from the infant 44.

Accordingly, a removable ear insert 46 is hereby provided for insertion into an ear 48 of a parent 42*a*, 42*b* needing to be awoken or alerted, the ear insert 46 providing an audible output to only the wearer thereof. It is thus recognized that while many persons share a bed with a spouse or other bed partner, or, alternatively, share a room with any other person or persons, only effected persons need to be alerted to various audible parameters, including audible parameters from the infant 44 in the infant's room 16, whereby only the wearer of the ear insert 46 is awoken without disturbing others nearby the wearer, such as others in a room like the parents' room 18 who are not wearing the ear insert 46. By inserting the ear insert 46 into an ear 48 prior to slumber, for example, only the wearer is preferably awoken by the audible parameter from the infant 44, whereby no-one else is alerted due to the absence of a globally broadcast audible parameter emanating from the loudspeaker and sound grating 32 of the conventional PMD 14.

Thus, according to a preferred embodiment of the invention, individuals near the wearer are not exposed to, or otherwise made aware of, the audible parameter from the infant 44. Whereby the ear insert 46 is worn within the ear 48 of the wearer, any audio stimulus from the IMD 12 is preferably personal to the wearer and does not disturb others around the wearer, including, for example, the wearer's bed partner. Thus, the invention provides an ear insert 46 that is comfortably inserted into and worn within the ear 48 of the wearer for use in conjunction with an infant monitoring system 10. In other words, while the ear insert 46 is worn within the ear 48 of the wearer, the audible parameter from the infant 44 is received by circuitry within the ear insert 46 and preferably delivered privately to the wearer through the ear insert 46, whereby non-wearers of the ear insert 46 remain undisturbed.

Whereas the common loudspeaker in a conventional PMD 14 contains a cone that is rigidly attached to a coil of wire, as previously described, an earphone, such as the ear insert 46 of the present invention, preferably contains a diaphragm that is rigidly attached to the coil of wire. The ear insert 46 otherwise retains the functionality of the conventional PMD 14. For example, the coil of wire is still surrounded by a permanent magnet that creates a permanent magnetic field about the coil. As electrical current signals pass through the coil of wire, a varying magnetic field is again induced about the coil. The permanent and varying magnetic fields thus oppose, and otherwise interact, with one another, whereupon the diaphragm thus vibrates according to the variations in the electrical current signals. Successfully vibrating the diaphragm according to the voltage of the original electrical current signal transmitted from the IMD 12, the diaphragm thereby causes surrounding air to vibrate at the same frequencies as the original sound waves. This sound is then broadcast through the ear insert 46 and into the ear 48 of the wearer. Accordingly, the ear insert 46 wirelessly reproduces the audible parameter received by the IMD 12 in the infant's room 16 through the ear insert 46 worn by the wearer. Other earphone and earphone-type devices are also well-known in the art, and expressly contemplated hereby.

In a preferred embodiment, the ear insert 46 is self-contained, i.e., it contains no wires, straps, mounting loops, or otherwise, in which the wearer can become entangled. Accordingly, a preferred ear insert 46 is powered by a conventional power source such as a battery, battery cell, or otherwise. Moreover, the preferred ear insert 46 is molded to fit securely and comfortably within the wearer's ear 48 during slumber, or when doing other jobs or activities within the transmission and reception ranges of the infant monitoring system 10. Accordingly, when the ear insert 46 is inserted into the wearer's ear 48 and energized, reproduced sounds from the IMD 12 are preferably heard personally by the wearer. Thus, the ear insert 46 is a miniaturized PMD 14, possessing the functionality thereof.

Figure 3:
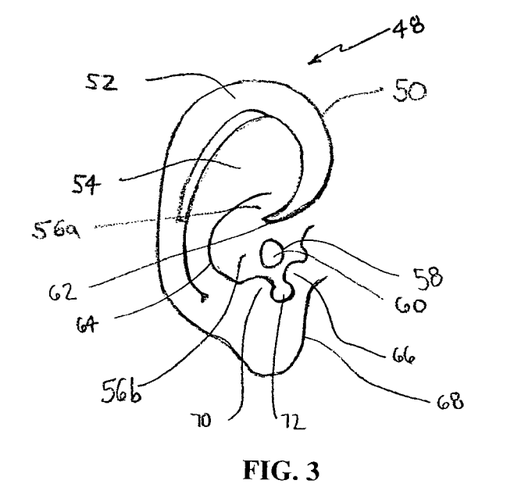
FIG. 3 depicts relevant parts of a typical human ear.
Figure 4:
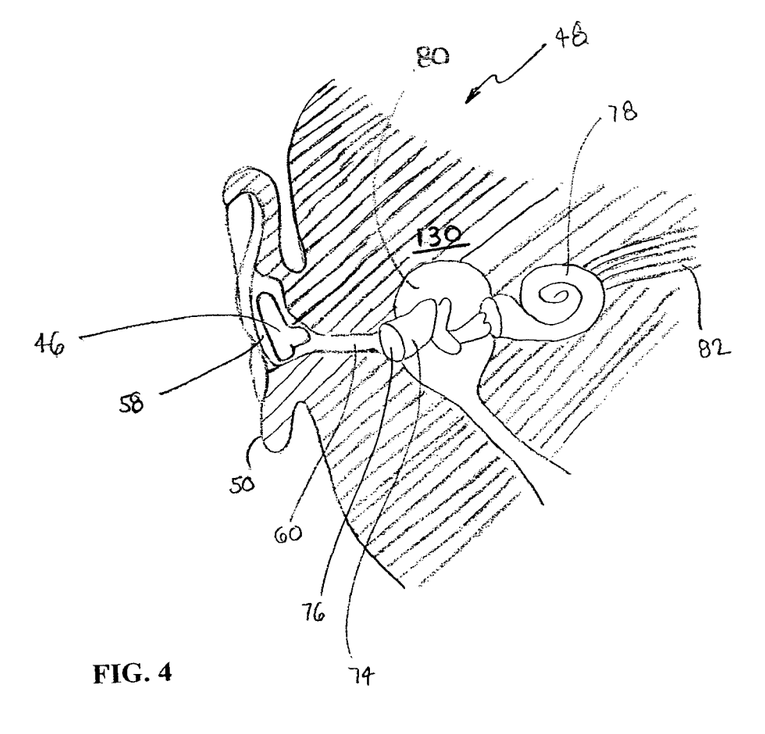
FIG. 4 depicts a cross-sectional view of an ear insert positioned in an ear of a wearer according to preferred embodiments of the inventive arrangements.

For illustration purposes, and to elaborate upon preferred placement and positioning of the ear insert 46 within the ear 48, a typical human ear 48 is depicted in FIGS. 3–4. Referring more specifically to FIG. 3, the outer ear 50 (i.e., pinna) comprises an irregularly concave cartilaginous member comprised of a number of eminencies and depressions that provide a distinctive shape and form to the ear 48. More specifically, a helix 52 comprises a curved outer rim of the ear 48. Below the helix 52 is an antihelix 54. The antihelix 54 comprises a curved prominence forming a curve around a concha 56, which is a deep cavity containing an entry passage 58 to an ear canal 60. The concha 56 is divided into two parts, including an upper concha 56a and lower concha 56b (collectively, 56). The upper concha 56a and lower concha 56b are divided into their respective parts by a terminating crux 62 of the helix 52 that curves around the outside of the ear 48 and extends inwards at about a vertical midpoint of the ear 48. The upper concha 56a lies above the crux 62 of the helix 52 and below the antihelix 54. The lower concha 56b, on the other hand, lies below the crux 62 of the helix 52 and surrounds the entry passage 58 to the ear canal 60. A conchal wall 64 separates the concha 56 from the antihelix 54. A tragus 66 comprises a small semicircular prominence disposed in front of the lower concha 56b and projecting rearwards from a front 68 of the ear 48. An antitragus 70 is disposed opposite the tragus 66 and separated apart therefrom by a deep curvature of an intertragic notch 72, which is formed between the tragus 66 and antitragus 70.

Referring now more specifically to FIG. 4, the ear canal 60 connects the entry passage 58 to an ear drum 74. When sound, such as the audible parameter from the infant 44, enters the ear 48, a front surface 76 of the ear drum 74 vibrates. These vibrations then pass from the front surface 76 of the ear drum 74 to a cochlea 78 within an inner ear 80, the inner ear 80 generally being defined as beginning at about the entry passage 58 to the ear canal 60. The cochlea 78 converts vibrations on the surface 76 of the ear drum 74 into electrical signals, which travel along an auditory nerve 82 to a brain (not shown) for interpretation and processing as audible sound by the wearer of the ear insert 46.

As can now be seen, the removable ear insert 46 preferably fits comfortably within the wearer's ear 48. More specifically, it contacts and preferably fits within the outer ear 50 of the wearer. Even more specifically, it preferably fits within the concha 56 of the outer ear 50 of the wearer. Yet even more specifically, it is preferably positioned at the entry passage 58 to the ear canal 60.

As described, the ear insert 46 is preferably suitable for insertion into the wearer's ear 48. Alternatively, the ear insert 46 is suitable for covering the wearer's ear 48, in which case the ear insert 46 is preferably suitable to cover the outer ear 50 of the wearer, or is suitable for mounting on the wearer's ear 48. In such embodiments, covering and mounting are readily accomplished by techniques well-known in the art.

Preferably, the ear insert 46 is molded to match the contour of an average ear 48 in one embodiment. Alternatively, it is preferably custom-molded to match the contours of a specific wearer's ear 48 in an alternative embodiment.

Preferably, the ear insert 46 is an electromagnetic or piezo-electric type of earphone device, such as commonly used in hearing aids, and well-known in the art.

Preferably, it is implemented in the form of a molded ear insert 46. More specifically, the ear insert 46 is preferably implemented in the form of a molded ear insert 46 that is made of plastic, rubber, silicone, or other material suitable for being inserted into a wearer's ear 48. Preferably, it is suitably encased in a plastic, rubber, silicone, or other material housing.

Preferably, it is outfitted with, i.e., surrounded by, either in part or in whole, a cushioning member that is cloth, foam, rubber, foam rubber or the like to enhance comfort for the wearer.

Preferably, it shaped to fit within either a wearer's left or right ear 48, or both.

Preferably, it is sized to minimize slippage or movement within the wearer's ear 48. For example, in one preferred embodiment, the ear insert 46 fits snugly within the concha 56 of the wearer. In the same or an alternative embodiment, it fits snugly within abutting contact of the conchal wall 64. In the same or additionally alternative embodiments, it fits snugly between the tragus 66 and antitragus 70. In the same or additionally alternative embodiments, it is lodged securely among one or more of the following: the conchal wall 64, tragus 66, antitragus 70, and intertragic notch 72.

Preferably, it is dimensioned to inhibit ambient noises and other external sounds typical of a household setting. For example, when one or both of the parents 44a, 44b utilize the ear insert 46 not only during slumber but also while performing other tasks, such as housework, mowing a yard, and the like, whereas before, hearing the audible parameter from the infant 44 would have otherwise been difficult or suspect due to ambient noises and other external sounds, whereby now, such audible parameters from the infant 44 are readily discernable. In the foregoing embodiment, the ear insert 46 is appropriately sized and dimensioned to fill the outer ear 50 such that sounds other than the audio parameter from the infant 44 are inhibited or altogether precluded from entering the inner ear 80 of the wearer. This embodiment is preferably accomplished by sizing the ear insert 46 to substantially fill the concha 56 of the outer ear 50. Other applicable techniques are also well-known in the art.

Preferably, the ear insert 46 projects sound internally. More specifically, it projects sound internally towards the inner ear 80. Even more specifically, it projects sound internally towards the inner ear 80 through the entry passage 58 to the ear canal 60. Yet even more specifically, it projects sound internally towards the inner ear 80 through the entry passage 58 to the ear canal 60 and towards the ear drum 74, cochlea 78, and auditory nerve 82. In other words, it is preferably removably positioned to point and project sound inwards relative to the inner ear 80 and outer ear 50. Accordingly, it preferably projects sound internally towards the ear drum 74 of the inner ear 80.

In other preferred embodiments, various modifications to the foregoing are also possible. For example, in one preferred embodiment of the foregoing, each of the parents 42 wear a separate ear insert 46 to monitor more than one infant 44 making more than one audible parameter in more than one infants' rooms 16. In such an embodiment, the infant monitoring system 10 preferably utilizes more than one infant monitoring device 12. In still other preferred embodiments, the ear insert 46 preferably includes conventional PMD 14 functionality, including, for example, globally broadcasting audible parameters when both parents 42 need or desire to be alerted to the audible parameter from the infant 44. In still other preferred embodiments, the IMS 10 includes an IMD 12, PMD 14, and an ear insert 46. Thus, the parents 42 can use either the conventional PMD 14, preferably placed on the bed-side table 40, or, alternatively, one of the parents 42 can wear the ear insert 46. This embodiment allows full functionality of the IMS 10, whereby the IMD 12 can transmit directly to the PMD 14, to the ear insert 46, or to both. In another preferred embodiment, the IMD 12 transmits to the PMD 14, which in turn, transmits to the ear insert 46.

It should be understood that this Specification describes exemplary, and therefore non-limiting, embodiments of the invention. Accordingly, the scope of the present invention is not limited to any of these embodiments. Rather, these embodiments were disclosed as required. Thus, many changes and modifications—as apparent to those skilled in the art—are within the scope of the invention without departing from the spirit hereof, and the inventive arrangements are inclusive thereof. Thus, to further apprise the public of the scope of this invention, the following claims are hereby made:

What is claimed is:

1. An infant monitoring system comprising a wireless removable ear insert for providing an audible parameter from a remote infant monitoring device to a wearer of said insert, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

2. The system of claim 1 wherein said insert provides said parameter only to said wearer of said insert and not to non-wearers of said insert.

3. The system of claim 1 wherein said insert is wearable within abutting contact of an ear of said wearer.

4. The system of claim 1 wherein said insert is dimensioned to fit within an outer ear of said wearer.

5. The system of claim 1 wherein said insert is wearable within an outer ear of said wearer.

6. The system of claim 1 wherein said insert is dimensioned to fit within a concha of an ear of said wearer.

7. The system of claim 1 wherein said insert fits within a right ear of said wearer or a left ear of said wearer.

8. The system of claim 1 wherein said insert fits within a right ear of said wearer and a left ear of said wearer.

9. The system of claim 1 wherein said insert is dimensioned to minimize slippage within an ear of said wearer.

10. The system of claim 1 wherein said insert is molded to match a contour of an average outer ear of said wearer.

11. The system of claim 1 wherein said insert is custom-molded to match a contour of a specific outer ear of said wearer.

12. The system of claim 1 wherein said insert is positionable at an entrance portion of an ear of said wearer.

13. The system of claim 1 wherein said insert is positionable at an entry passage to an ear canal of said wearer.

14. The system of claim 1 wherein said insert directs said parameter towards an ear drum of said wearer.

15. The system of claim 1 wherein said insert isolates an ear of said wearer from an external environment relative to said ear.

16. The system of claim 1 wherein said system provides said parameter to said wearer based on a comparison of said parameter by a comparator.

17. The system of claim 16 wherein said comparison is relative to one or more predetermined reference parameters.

18. The system of claim 16 wherein said insert contains said comparator.

19. The system of claim 16 wherein said remote infant monitoring device contains said comparator.

20. The system of claim 1 wherein said insert covers an outer ear of said wearer.

21. The system of claim 1 wherein said insert mounts on an ear of said wearer.

22. The system of claim 1 wherein said insert provides said parameter such that said parameter is personal to said wearer.

23. The system of claim 1 wherein said insert provides said parameter such that said parameter is personally hearable by said wearer.

24. The system of claim 1 wherein said insert provides said parameter such that said parameter is personal to said wearer and personally hearable by said wearer.

25. The system of claim 1 wherein said parameter comprises a personal alert to said wearer.

26. The system of claim 1 wherein said insert provides an audio output to said wearer.

27. The system of claim 26 wherein said audio output is based on said parameter.

28. The system of claim 1 wherein said insert and said remote infant monitoring device are in electrical communication.

29. The system of claim 1 wherein said remote infant monitoring device contains a microphone for receiving said parameter.

30. The system of claim 1 wherein said remote infant monitoring device contains a transmitter for transmitting said parameter to said insert.

31. The system of claim 1 wherein said remote infant monitoring device contains a microphone for receiving said parameter and a transmitter for transmitting said parameter to said insert.

32. The system of claim 1 wherein said remote infant monitoring device contains a microphone for receiving said parameter and a transmitter for transmitting said parameter to said insert.

33. The system of claim 1, wherein said insert is made from a material selected from a group consisting of plastic, rubber, and silicone.

34. The system of claim 1 wherein said insert is of a type selected from a group consisting of electro-magnetics and piezo-magnetics.

35. The system of claim 1 wherein said insert contains a surrounding cushioning member to enhance comfort for said wearer.

36. The system of claim 35 wherein said cushioning member is selected from a group consisting of cloth, foam, rubber, and foam rubber.

37. An infant monitoring system comprising one or more removable ear inserts for providing one or more audible parameters from on or more remote infant monitoring devices to one or more wearers of said one or more inserts, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

38. An infant monitoring system comprising an infant monitoring device in electrical communication with a remote parent monitoring device, the parent monitoring device being a removable ear insert for providing an audible parameter from said infant monitoring device, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

39. An infant monitoring system comprising an infant monitoring device in electrical communication with a remote parenting monitoring device and an ear insert, the infant monitoring device providing an audible parameter from said infant monitoring system to either or both of the parent monitoring device and ear insert, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

40. A method for providing a personal alert to a caregiver comprising:

providing an infant monitoring system having a removable wireless ear insert, and providing an audible parameter from a remote infant monitoring device to a wearer of said insert, wherein said insert is a self-contained insert which includes a receiver for receiving said parameter from said remote infant monitoring device and a transducer for converting said parameter into sound energy, and wherein said insert is formed to fit securely to fit securely and comfortably within a concha of a wearer's ear without requiring any straps or mounting loops.

41. A personal monitoring system comprising a removable wireless ear insert for providing an audible parameter from a remote monitoring device monitoring an infant or the like to a wearer of said insert, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

42. A removable wireless ear insert for use with an infant monitoring system comprising means for providing an audible parameter from a remote infant monitoring device to a wearer of said insert, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

43. A removable wireless ear insert for use with a personal monitoring system comprising means for providing an audible parameter from a remote monitoring device monitoring an infant or the like to a wearer of said insert, wherein said insert is a self-contained insert including a receiver for receiving said parameter from said remote infant monitoring device, a transducer for converting said parameter into sound energy, and a power source to power the receiver and the transducer, and wherein said insert is formed to fit securely to fit securely and comfortably within a concha of a wearer's ear without requiring any straps or mounting loops.

* * * * *